(12) United States Patent
Tregoat et al.

(10) Patent No.: US 7,977,063 B2
(45) Date of Patent: Jul. 12, 2011

(54) METHOD FOR DETERMINING AN ALLERGIC RESPONSE

(75) Inventors: Virginie Sophie Christelle Tregoat, Geel (BE); Johan Garssen, Nieuwegein (NL)

(73) Assignee: N.V. Nutricia, Zoetermeer (NL)

( * ) Notice: Subject to any disclaimer, the term of this patent is extended or adjusted under 35 U.S.C. 154(b) by 672 days.

(21) Appl. No.: 11/908,773

(22) PCT Filed: Mar. 16, 2005

(86) PCT No.: PCT/NL2005/000199
§ 371 (c)(1),
(2), (4) Date: Sep. 14, 2007

(87) PCT Pub. No.: WO2006/098612
PCT Pub. Date: Sep. 21, 2006

(65) Prior Publication Data
US 2008/0145871 A1 Jun. 19, 2008

(51) Int. Cl.
G01N 33/00 (2006.01)

(52) U.S. Cl. ....... 435/7.24; 435/353; 435/372; 435/383; 435/392; 436/506; 436/507; 436/513; 436/15; 436/20; 436/21; 436/22; 436/23; 436/35; 436/63

(58) Field of Classification Search .................. 424/9.2; 435/2, 4, 372, 383, 392, 7.24, 353; 436/506, 436/507, 513, 519, 15, 17, 20–23, 35, 63, 436/147; 530/387.1, 387.3
See application file for complete search history.

(56) References Cited

U.S. PATENT DOCUMENTS

| 4,559,310 A | 12/1985 | Cantor et al. | |
| 5,714,338 A * | 2/1998 | Wai Fei et al. | 435/7.24 |
| 2003/0022250 A1* | 1/2003 | Dreskin et al. | 435/7.21 |

FOREIGN PATENT DOCUMENTS

| WO | WO 93/25904 A | 12/1993 |
| WO | WO 94/12876 A | 6/1994 |
| WO | WO 95/15494 A | 6/1995 |

OTHER PUBLICATIONS

Aketani et al., "Correlation between cytosolic calcium concentration and degranulation in RBL-2H3 cells in the presence of various concentrations of antigen-specific IgEs," *Immunology Letters*, Jan. 15, 2001, pp. 185-189, vol. 75, No. 3.

Dibbern et al., "RBL cells expressing human RcRI are a sensitive tool for exploring functional IgE-allergen interactions: studies with sera from peanut-sensitive patients," *Journal of Immunological Methods*, Mar. 1, 2003, pp. 37-45, vol. 274, No. 1-2, Elsevier Science Publishers B.V., Amsterdam, NL.

* cited by examiner

*Primary Examiner* — Gail R Gabel
(74) *Attorney, Agent, or Firm* — Gilberto M. Villacorta; Sunit Talapatra; Foley & Lardner, LLP

(57) ABSTRACT

The present invention concerns a method for determining an allergic response by determining the extent of degranulation of human IgE sensitized cells upon activation by allergens in food products.

13 Claims, No Drawings

METHOD FOR DETERMINING AN ALLERGIC RESPONSE

FIELD OF THE INVENTION

The present invention is in the field of allergy, in particular food allergy. The invention provides an in vitro method for determining whether or not a subject will show an allergic response when challenged with a particular food product. The present invention also provides a method developing food products with a favorable allergy profile.

BACKGROUND OF THE INVENTION

Food allergy is a detrimental immunoreaction in susceptible individuals that is caused by ingestion of an allergy-inducing substance in a food and can cause dermatitis, asthma, digestive-tract obstacle, anaphylactic shock, etc. Food allergy is primarily a so-called type I allergy, i.e. an immunological disorder mediated by IgE antibodies in which IgE antibodies react with food allergens taken inside the body. The number of food-allergy patients has been increasing in recent years and the phenomenon of food allergy causes serious problems in medical fields and in the food industry.

Allergy-inducing foods include eggs, milk, meat, fish, the crustaceans and mollusks, cereals, legumes and nuts, fruits, vegetables, gelatin, yeast (beer) etc. Similarly, ovoalbumin, ovomucoid, lysozyme, casein, beta-lactoglobulin, alpha-lactoalbumin, gluten, alpha-amylase inhibitor, etc. are known as allergy-inducing food constituents.

The diagnosis of food allergies is one field where many deficiencies still exist, regardless of the development of various tests. In many cases, the patients themselves notice a connection between their symptoms and certain allergens, for example by observing an immediate adverse reaction upon ingestion of the suspected allergen or by eliminating and re-introducing the source of allergens. A detailed anamnesis is therefore often very helpful in establishing a diagnosis.

Diagnosis of food allergy is performed in several, partly complementary ways. In addition to an anamnesis, the diagnosis can further be supported by in vivo measurements and in vitro assays. As in vivo technique a skin test with food allergen extracts is most common. Sometimes an oral provocation is necessary to determine which food components are the causative agents of the observed allergy. Methods for developing food products with a favorable allergy profile require double blind, placebo-controlled food challenge tests. The most common in vitro tests are RAST and ELISA. In these assays, extracts of potentially allergic, antigenic material are immobilized to a solid phase (e.g. Sepharose, magnetic particles, polystyrene plates, etc.). After incubation of the solid phase with serum of a patient, the binding of specific IgE antibodies is usually measured.

In particular the ELISA method suffers several drawbacks. For example the method cannot always detect allergens that food allergy patients are sensitive to. In other words, they cannot always detect substances that are recognized by IgE antibodies of the patients. Also the method can only detect known allergens, and a single allergen per method. Further the method using single antigen-detecting antibodies are not applicable to inspection of allergy-inducing foods containing no known antigen (e.g. a method using a single antibody prepared by exposure to ovalbumin localized in egg white is not applicable to inspection of egg yolk and for example egg yolk mayonnaise, etc.). The method using single antigen-detecting antibodies are not applicable to inspection of the processed foods, because they cannot detect denatured or molecule-modified allergens.

Thus many allergens have been identified and in some cases isolated and characterized down to molecular levels. In practice, however, it is often enough to identify a particular food stuff as source of allergens, e.g. cow milk containing several known allergenic proteins.

When it comes to provocation tests problems arise in specific situations, e.g. where the allergic reaction is either delayed, very diffuse or part of a complex of clinical symptoms. In the first case, when the reaction is delayed, it becomes difficult to associate the problems with the particular food causing them. Often, the symptoms resemble the symptoms of common problems such as headache, fatigue and joint pains. It is also possible that the same substances produce different reactions or at least fail to produce an identical reaction every time. It is understandable that the establishing of a diagnosis is both difficult, time-consuming and often frustrating for both the physician and the patient.

Besides this, in critically ill patients a provocation test is the last thing a physician would want to do. Moreover, it will probably be impossible to reliably relate, and this is even more the case where infants, and more in particular critically ill infants are concerned, a clinical symptom or complaint to a true allergic response.

Takagi et al. (2003) Biol. Pharm. Bull. vol 26(2), p 252 describe the application of human FcεRI α-chain-transfected RBL-2H3 cells for detecting receptor bindable serum IgE. The transfected cells were sensitized with heat-inactivated serum from allergic patients and stimulated with anti-human IgE antibody. Ambivalent results were obtained in a β-hexosaminidase assay for determining degranulation in samples having different dilution of sera. No particular interest is directed at food allergy.

Aketami et al. (2001) Immunology Letters vol 75, p 185 correlated calcium concentration and degranulation measured by the β-hexosaminidase assay in a RB-2H3 cell system sensitized with serum specific for chicken egg albumin generated in mice.

Dibbern et al. J. Immumunological Methods, (2003) vol 274, p 37 describe RBL cells expressing the complete human FcεRI receptor. Degranulation of such cells sensitized with sera from peanut-sensitive patients upon activation with peanut allergens was measured by determining tritium labelled serotonin.

SUMMARY OF THE INVENTION

It has now been found that it is possible to determine the allergic response to a food product in a subject with an in vitro assay by sensitizing cells that are capable of degranulation with a sample comprising serum from said subject. Upon incubation of the sensitized cells with for example a food product it is possible to determine that said subject has an IgE mediated response to an allergen or allergens contained in said food product by determining the extent of degranulation of the sensitized cells.

A major advantage of the present method is that it is now possible to test the allergic response to a 'complete' food product. Such a method is particularly suited for subjects of which it is not (yet) known whether or not there is an allergic response to food allergens and which are in a critically ill state. An allergic reaction to a food product in these patients may inflict more stress leading to more severe illness or even death. Hence, determining if these subjects are allergic or determining which food product gives a favorable allergic response is important if critically ill patients are admitted to a hospital. Furthermore, a group of subjects that will not have a well documented history of food allergy are infants and the method of the invention is particularly advantageous for this group, the more so if the infants are critically ill and are for example admitted to a hospital. Hence, the present method is particularly suitable for testing nutritional complete food products, such as infant milk formula, tube-fed nutritional formula and clinical nutrition.

Another advantage of the present method is in the field of product development. By pooling sera from a group of subjects from which it is known they have an allergy to for instance milk, a combined serum having a great variety of allergy-specificities is obtained. By sensitizing cells that are capable of degranulation with this pooled serum and testing different food compositions for the extent of degranulation, a food composition with the most favorable allergy profile can be developed.

Thus the invention relates to a method for determining an allergic response in a subject, said method comprising the steps of
a) incubating cells capable of degranulation with an aqueous solution comprising human IgE to obtain sensitized cells
b) incubating the sensitized cells obtained in step a) with an allergen comprising a component selected from the group consisting of one or more components from milk, egg and fruit.
c) determining the extent of degranulation.

In another aspect the invention relates to a method for developing a food product having a favorable allergy profile, said method comprising the steps of
a) incubating cells capable of degranulation with an aqueous solution comprising human IgE to obtain sensitized cells
b) incubating the sensitized cells obtained in step a) with a food composition
c) determining the extent of degranulation
d) optionally repeating steps a), b) and c) if the allergy profile of the product is not favorable, wherein in step b) a different food composition is used
e) optionally repeating step d) one or more times until a food product having a favorable allergy profile is obtained.

The present invention also concerns a kit of parts for carrying out the method according to the invention, said kit comprising at least one nutritional composition containing milk, egg or fruit and degranulation detection means selected from the group consisting of means to determine the extracellular and/or intracellular $Ca^{2+}$ concentration, means to perform isotope assays, and/or means to determine β-hexosaminidase activity.

DETAILED DESCRIPTION

Cells

Cells capable of degranulation are prominently considered to be mast cells and blood basophils. Degranulation is a primary event in an allergic condition. The binding of IgE antibodies to high-affinity IgE receptors on the surface of mast cells and basophils and subsequent crosslinking of the receptors are the first steps in the degranulation process where the substances that cause type I allergy are released. Thus stable human cell lines of mast cells and basophils are suitable cells in the present method. At present such cell lines are not readily available and need to be prepared from freshly collected peripheral blood or developed from human cord blood $CD34^+$ progenitor cells. It is therefore preferred such cells are immortalized e.g. by fusion with a carcinoma cell line.

A key factor in the cells that are capable of degranulation is the presence of the IgE receptor, in particular FcεRI, which is usually expressed in tetrameric form ($αβγ_2$) or trimeric form ($αγ_2$). Preferably at least part of the IgE receptor is capable of binding human IgE (hIgE). The α-chain binds IgE and the γ-chain transduces signals. It has already been shown that non-human basophils are able to show human IgE-dependent degranulation when the non-human basophils are transfected with the α-, β- and γ-chains of the human FcεRI (Dibbern et al. supra) and even with only the α-chain of FcεRI (Takagi et al supra). In particular the non-human basophils are basophils from a rodent, preferably from a rat and in particular are rat basophilic leukemia cells (RBL).

Thus in one embodiment the cells capable of degranulation are basophilic cells transfected with human FcεRI, preferably transfected with the α-chain of human FcεRI. In another embodiment the cells capable of degranulation are from a rodent, preferably the cells are RBL-cells.

Sensitization

In the method of the invention an aqueous solution comprising human IgE is used to sensitize the cells capable of degranulation. Preferably the aqueous solution comprises serum from a subject, preferably serum from a human subject, more preferably serum from an infant. In order to assess if a food product comprises allergens, for example in the development of food products with a focus on favorable properties in terms of allergy, it is advantageous to use serum from a pool of subjects, i.e. a pool of sera, in particular from subjects known to have an allergy for a particular food product.

Allergens

Contrary to the present perception that when diagnosing for an allergy in a subject purified or isolated allergens should be used, the present method offers the possibility of assessing the allergic response to a whole food product. This is particularly useful when testing for allergies for food products that contain a great number of components with multiple allergy inducing epitopes. The present method can also be suitably used to select a nutritional product which induces limited allergic reaction from a variety of nutritional products. Specifically the present method is therefore suitable for determining the allergic response to allergens that are present in milk, eggs and fruit and thus to food products based on milk, eggs or fruit or food products containing these ingredients.

In a particular preferred embodiment, the allergic reaction of a complete nutritional composition is tested, i.e. a product containing protein, carbohydrate and optionally fat. The nutritional composition is preferably tested in powder or in liquid form, and contains preferably between 2 and 50 wt. % protein based on dry matter, between 10 and 90 wt. % carbohydrate based on dry matter, optionally between 5 and 50 wt. % lipid based on dry matter, vitamins, and preferably also minerals. Nutritional compositions containing milk proteins, preferably at least 1 wt. % milk protein based on dry weight of the nutritional composition, particularly casein, whey and/or hydrolyzed milk protein, are preferably used in the present method.

Degranulation

In the art several methods exist to assess degranulation. Characteristic for the granules that are released form the mast cells and basophils is that they contain β-hexosaminidase, serotonin and histamine. The release of granules is a calcium dependent process. Biochemical changes that occur during the degranulation of mast cells and basophils include the mobilization of $Ca^{2+}$, enhanced phospholipid metabolism, release of arachidonic acid, cyclic AMP production and the activation of protein kinases. In the method of the invention any assay that can measure any of the abovementioned processes is suitable. In particular it may be suited to determine the extracellular and/or intracellular $Ca^{2+}$ concentration (Aketani et al. supra), and/or perform isotope assays such as for instance determining the presence of tritium labeled serotonin (Dibbern et al. supra), and/or to determine β-hexosaminidase activity (Takagi et al. supra; Marchand et al. Allergy (2003) 1037) as a measure for the extent of degranulation. β-hexosaminidase activity is preferably determined using 4-methyl umbelliferyl-N-acetyl-β-D glucosaminide; extracellular and/or intracellular $Ca^{2+}$ concentration is preferably determined using Fura-2 AM (see below); in the isotope assay preferably [$^3$H]5-hydroxytryptamine is used.

Conveniently the extent of degranulation is expressed as a percentage relative to a "positive" control (sensitization with pure human IgE and stimulation with anti human IgE) which is set at 100%.

In general it will be clear to the skilled person when an allergy profile is considered favorable. As a rule of thumb it can be said that an allergy profile is not favorable if the extent of degranulation is significantly greater than the degranulation measured in the same degranulation assay for an appropriate negative control sample, i.e. usually a sample of serum of a non-allergic subject or a pool of sera from non-allergic subjects. A preferred measure of a favorable allergy profile is that the extent of degranulation is less than 50%, preferably less than 30% of the extent of degranulation of a positive control, i.e. usually purified IgE, in the same assay.

The same principles apply for determining if a subject displays an allergic response to a food product. It can be said that a subject shows an allergic response if the extent of degranulation is at least 30%, preferably at least 50%, of the extent of degranulation of a positive control, i.e. usually purified IgE, in the same assay. It is preferred to say that a subject shows an allergic response if the extent of degranulation is significantly greater than the degranulation measured in the same degranulation assay for an appropriate negative control sample, i.e. usually a sample of serum of a non-allergic subject or a pool of sera from non-allergic subjects.

Subjects

The present method is particularly suitable for determining an allergic response in children with the age between 0 and 10 years, preferably infants with the age between 0 and 4 years. The present method can advantageously be used for determining an allergic response in infants from 6 to 36 months. Hence, the present method can also be suitably used for recommendation of the best nutrition for the individual infants by infant welfare centers.

Also the present method is particularly suited for determining the allergic response of critically ill patients to a food product. In a further preferred embodiment, the present method can be used to prevent anaphylactic shock in patients. Preferably the aqueous solution to be tested comprises serum from patients suffering from asthma, cardiac diseases, diabetes and/or atherosclerosis. These patients particularly suffer from the disadvantageous effects of an allergic reaction.

Kit of Parts

In a further aspect the present invention provides a kit of parts that can be suitably used in the method mentioned hereinbefore. The kit of part comprises at least one nutritional composition, preferably at least two, more preferably between 3 and 10; and means to determine the extracellular and/or intracellular $Ca^{2+}$ concentration and/or perform isotope assays, and/or to determine β-hexosaminidase activity. The nutritional composition(s) is preferably provided in a quantity between 0.1 and 100 gram per nutritional composition. Preferably the kit of parts contains a component suitable for use in one of the assay selected from the group consisting of 4-methylumbelliferyl-N-acetyl-β-D-glucosaminide, Fura-2 AM and [$^3$H]5-hydroxytryptamine. Fura-2 AM is 1-[6-Amino-2-(5-carboxy-2-oxazolyl)-5-benzofuranyloxy]-2-(2'-amino-5'-methylphenoxy)-ethane-N,N,N',N'-tetra-acetic acid penta-acetoxymethyl ester (CAS Number: 108964-32-5).

In one embodiment the degranulation detection means can be replaced by instructions to measure degranulation in the method according to this invention or the kit can be supplemented with such instructions. In yet another embodiment the nutritional composition may be a replaced by a series of at least two or more compositions said series of compositions providing a representative picture of known allergens. Such a series of compositions thus need not be composed of nutritional compositions per se, but such a series of compositions may comprise pure or isolated or individual epitopes giving rise to allergic responses.

EXAMPLES

Example 1

Degranulation Induction with Serum Allergic and Non-Allergic Patients

Degranulation Model for Product Development and Substitution to Allergy Typing

The following system can be used for food allergen detection as well as determination of the reactivity of allergic patients.

Assay:

The degranulating cells are cultured in Geneticin free medium (selective marker) for 1-2 days and are sensitized overnight with a source of IgE (purified, individual sera and/or pool sera), preferably in a dilution range. In case of product development the sera would be preferentially isolated from allergic patients and especially cow's milk or egg allergic donors. The corresponding cells loaded with IgE are washed several times with a PIPES buffer (and or Tyrode buffer) to get rid of the unbound IgE. The cells are further stimulated for 30 min to 1 hour with the allergen, which can be pure allergen but preferably commercial food products of food compositions under development are used. Typical allergen concentrations range from 0-1000 ng/ml. The supernatant of the stimulated cells is transferred into a 96 well plate specific for fluorescence measurement and incubated for 30 min to 1 hour at 37° C. with the substrate 4-methyl umbelliferyl-N-acetyl-β-D glucosaminide. The reaction is stopped with glycine buffer and fluorescence is evaluated with a fluorescence plate reader at an excitation of 360 nm and emission 460 nm.

RBL-2H3 cell line transfected with the α-chain of human FcεRI as described in Takagi et al. (2003) Biol. Pharm. Bull. 252, were used. As a proof of principle the assay system described above has been set up with pure food components. Next the set-up was used for the detection of allergy to food products in some commercial products (such as Nutrilon® infant nutrition).

Food allergens, essentially milk and its derivatives (caseins, whey proteins etc.) were tested. Degranulation is expressed in percentage relative to the positive control used at a constant concentration (pure human IgE).

Individual sera as well as pooled sera were tested in a dilution range of 1/50-1/320. In these dilution intervals, the degranulation is dose dependent for a constant concentration of allergen. Inversely, non-allergic sera used to sensitize the degranulating cells did not trigger degranulation after the addition of the allergen whatever the dilution tested.

Furthermore the degranulation observed with allergic sera is a dynamic phenomenon where the stimulated cells stay in good shape; the cells remain viable.

The whole degranulation assay fulfilled all the controls. Cells in the presence exclusively of either the IgE source or the allergen did not show degranulation above background. The antibiotics (penicillin/streptomycin) always present in culture media also did not show a significant interference in the detection of the in vitro system described.

The results obtained when testing a commercial product are summarized in table 1 wherein the values are expressed as a percentage relative to the "positive" control (sensitization with pure human IgE and stimulation with anti human IgE) which was set at 100%.

TABLE 1

| | Stimulation | | | |
|---|---|---|---|---|
| Sensitization | Anti human IgE | Milk | Commercial product (Nutrilon) | Commercial product defatted (Nutrilon) |
| Purified human IgE | 100% | | | |
| Individual cow's milk allergic sera | | 53% | 62% | 79% |
| Pool sera from CMA patients | | 99% | 84% | 91% |
| Non allergic sera | | 18% | 16% | — |

When comparing the different groups, the degranulation induced with cells sensitized with either individual allergic sera or pool sera was statistically different (p<0.005 and p<0.0001 respectively) to the background degranulation observed with the non-allergic sera. This significant difference was determined with total milk as well as for the food commercial product (Nutrilon®).

Example 2

Degranulation Induction with Serum of Patients Allergic to Cows Milk (CMA), Serum of Allergic Patients, but not to Cows Milk and Non-Allergic Patients The method was performed as described in Example 1. The results are depicted in Table 2 and show that the method can be suitably used for detection of allergic reactions of individual patients to nutritionally complete products. The serum of an allergic patient, but not to cows milk, does give a negative result, indicating the reliability of the present method.

TABLE 2

| | Stimulation | | |
|---|---|---|---|
| Sensitization | Anti human IgE | Milk (100 ng/ml) | Commercial product (Nutrilon) (100 ng/ml) |
| Purified human IgE | 100% | | |
| Non allergic sera | | 13% | 16% |
| Allergic patient but not specific to CMA (atopic) | | 12% | 24% |
| Pool sera from CMA patients | | 103% | 132% |

Example 3

Kit of Parts

Kit of Parts Containing:
a. A package containing 1 gram Nutrilon 2™ (Nutricia, Zoetermeer, Netherlands)
b. A package containing 1 gram Nutrilon Hypo-Allergeen™ (Nutricia, Zoetermeer, Netherlands)
c. A package containing 1 gram Neocate™ (Nutricia, Zoetermeer, Netherlands)
d. 4-methyl umbelliferyl-N-acetyl-β-D glucosaminide (from Fluka, Sigma-Aldrich)

The invention claimed is:

1. A method for determining an allergic response in a subject, said method comprising:
   a) incubating cells capable of degranulation with an aqueous solution comprising human IgE from the subject to obtain sensitized cells;
   b) incubating the sensitized cells obtained in step a) with a complete nutritional composition comprising an allergen component selected from the group consisting of milk, egg and fruit, between 2 and 50 wt. % protein based on dry matter, between 10 and 90 wt. % carbohydrate based on dry matter, and optionally, between 5 and 50 wt. % lipid based on dry matter; and
   c) determining the extent of degranulation, wherein an extent of degranulation of at least 30% relative to the extent of degranulation of a positive control provides indication of the allergic response in the subject to the allergen.

2. The method according to claim 1, wherein the cells capable of degranulation are selected from the group consisting of mast cells and basophilic cells.

3. The method according to claim 2, wherein the basophilic cells are transfected with the α-chain of human FcεRI.

4. The method according to claim 1, wherein the complete nutritional composition comprises between 5 and 50 wt. % lipid based on dry matter, and optionally vitamins.

5. The method according to claim 1, wherein the cells capable of degranulation are rodent cells.

6. The method according to claim 5, wherein the rodent cells are RBL-cells.

7. The method according to claim 1 wherein the aqueous solution further comprises serum.

8. The method according to claim 1, wherein the aqueous solution further comprises a pool of sera from a pool of the subjects.

9. The method according to claim 1, wherein the subject is a child from 0-10 years of age.

10. The method according to claim 9, wherein the subject is a child from 0-4 years of age.

11. The method according to claim 9, wherein the child is from 6 to 36 months of age.

12. The method according to claim 1, wherein in step b) the complete nutritional composition is a food product containing milk, egg or fruit or a food product based on milk, egg or fruit.

13. The method according to claim 1, wherein in step b) the complete nutritional composition is a food composition comprising, as a percentage of the total energy of the composition:
   (a) between 10 and 60% energy derived from lipid,
   (b) between 5 and 50% energy derived from protein and
   (c) between 15 and 90% energy derived from carbohydrate.

* * * * *